United States Patent
Wu et al.

(10) Patent No.: US 10,234,591 B2
(45) Date of Patent: Mar. 19, 2019

(54) CASING STRING MONITORING USING ELECTROMAGNETIC (EM) CORROSION DETECTION TOOL AND JUNCTION EFFECTS CORRECTION

(71) Applicant: HALLIBURTON ENERGY SERVICES, INC., Houston, TX (US)

(72) Inventors: Dagang Wu, Katy, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 178 days.

(21) Appl. No.: 15/118,998

(22) PCT Filed: Apr. 7, 2015

(86) PCT No.: PCT/US2015/024690
§ 371 (c)(1),
(2) Date: Aug. 15, 2016

(87) PCT Pub. No.: WO2015/157270
PCT Pub. Date: Oct. 15, 2015

(65) Prior Publication Data
US 2017/0038493 A1 Feb. 9, 2017

Related U.S. Application Data

(60) Provisional application No. 61/978,127, filed on Apr. 10, 2014.

(51) Int. Cl.
*G01V 3/28* (2006.01)
*G01N 17/04* (2006.01)
(Continued)

(52) U.S. Cl.
CPC ............ *G01V 3/28* (2013.01); *E21B 47/00* (2013.01); *E21B 47/0006* (2013.01); *E21B 47/0905* (2013.01); *G01N 17/04* (2013.01)

(58) Field of Classification Search
CPC .... E21B 47/00; E21B 47/0006; E21B 47/082; E21B 47/09–47/0915; G01V 3/18–3/34; G01N 17/04
See application file for complete search history.

(56) References Cited

U.S. PATENT DOCUMENTS 4,292,588 A 9/1981 Smith
4,292,589 A * 9/1981 Bonner ................. E21B 47/082
324/221
(Continued)

FOREIGN PATENT DOCUMENTS

WO 20110152924 12/2011
WO 2013/162505 10/2013
(Continued)

OTHER PUBLICATIONS

Extended European Search Report for Application No. 15777588.3-1559 dated Oct. 16, 2017.
(Continued)

*Primary Examiner* — Huy Q Phan
*Assistant Examiner* — David Frederiksen
(74) *Attorney, Agent, or Firm* — Benjamin Fite; C. Tumey Law Group PLLC

(57) ABSTRACT

A corrosion monitoring method includes obtaining electromagnetic (EM) log, data along a casing string. The method also includes processing the EM log data to estimate casing thickness of the casing string as a function of position, where the processing includes correcting, for junction effects in the casing string.

19 Claims, 6 Drawing Sheets

(51) Int. Cl.
*E21B 47/00* (2012.01)
*E21B 47/09* (2012.01)

(56) References Cited

U.S. PATENT DOCUMENTS

| | | | | |
|---|---|---|---|---|
| 6,012,526 | A * | 1/2000 | Jennings | E21B 7/061 166/297 |
| 6,483,777 | B1 | 11/2002 | Zeroug | |
| 2002/0100588 | A1 * | 8/2002 | Murray | E21B 41/0042 166/313 |
| 2002/0108754 | A1 * | 8/2002 | Hess | E21B 41/0035 166/313 |
| 2009/0091328 | A1 * | 4/2009 | Clark | G01V 3/28 324/338 |
| 2009/0195244 | A1 | 8/2009 | Mouget et al. | |
| 2009/0302852 | A1 | 12/2009 | Levesque et al. | |
| 2012/0095686 | A1 * | 4/2012 | Legendre | E21B 47/082 702/6 |
| 2013/0193953 | A1 | 8/2013 | Yarbro et al. | |
| 2016/0054467 | A1 * | 2/2016 | Li | G01V 3/18 702/7 |

FOREIGN PATENT DOCUMENTS

| | | |
|---|---|---|
| WO | 2014/011190 | 1/2014 |
| WO | 2015/157270 | 10/2015 |

OTHER PUBLICATIONS

Acuna, Alexandra Irlec et al., "Scanning for Downhole Corrosion", "Applying Electrical Micro-Imaging Logs to Reservoir Characterization" *Oilfield Review* 22, No. 1 (2010): 42-50.

Rourke, M., et al., "Multi-tubular Corrosion Inspection Using a Pulsed Eddy Current", *IPTC* 16645, Mar. 26-28, 2013, 6 pgs.

PCT International Search Report & Written Opinion, dated Jul. 8, 2015, Appl No. PCT/US2015/024690, "Casing String Monitoring Using Electromagnetic (EM) Corrosion Detection Tool," Filed Apr. 7, 2015, 12 pgs.

\* cited by examiner

CASING STRING MONITORING USING ELECTROMAGNETIC (EM) CORROSION DETECTION TOOL AND JUNCTION EFFECTS CORRECTION

CROSS-REFERENCE TO RELATED APPLICATIONS

The present application claims priority to U.S. Pat. App. 61/978,127 titled "Casing String Monitoring Using Electromagnetic (EM) Corrosion Detection Tool and Junction Effects Correction", filed Apr. 10, 2014 by inventors Dagang Wu and Burkay Donderici, which is incorporated by reference in its entirety.

BACKGROUND

For oil and gas exploration and production, a network of wells installations and other conduits are established by connecting sections of metal pipe together. For example, a well installation may be completed, in part, by lowering multiple sections of metal pipe (i.e., casing strings) into a borehole, and cementing the casing string in place. In some well installations, multiple casing strings are employed (e.g., a concentric string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, corrosion transfer, etc. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data can be interpreted to correlate a level of flux leakage or EM induction with corrosion. When multiple casing strings are employed together, correctly managing corrosion detection EM logging tool operations and data interpretation is not a trivial task.

BRIEF DESCRIPTION OF THE DRAWINGS

Accordingly, there are disclosed in the drawings and the following description various systems and methods for casing string corrosion monitoring using an electromagnetic (EM) logging tool and junction effects processing. In the drawings.

Figure 1A:
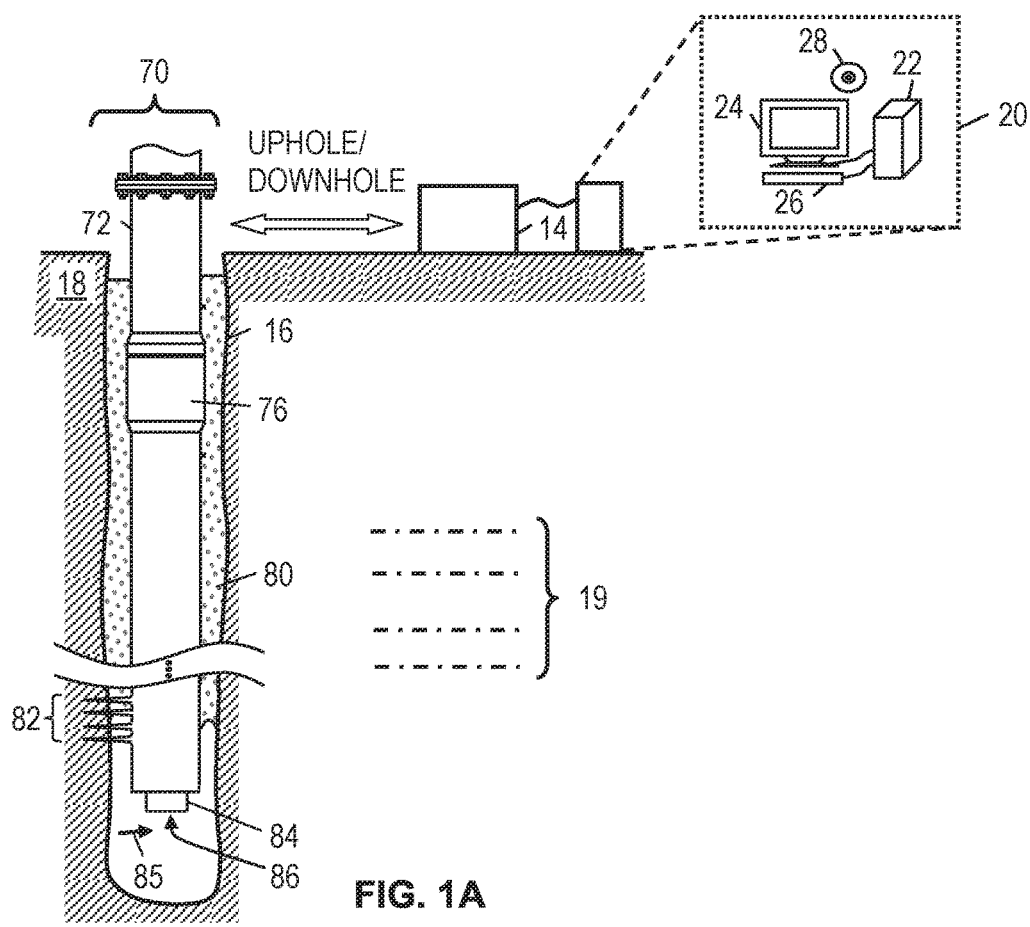
FIGS. 1A and 1B depict various illustrative casing string survey environments.

It should be understood, however, that the specific embodiments given in the drawings and detailed description do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Certain disclosed device, system, and method embodiments are directed to casing string corrosion monitoring using an electromagnetic (EM) logging tool and junction effects processing. In an example method, EM log data is obtained along a casing string. The method also includes processing the EM log data to estimate casing thickness of the casing string as a function of position, where the processing operations corrects for junction effects in the casing string. In some embodiments, the junction effects are corrected for using a multi-dimensional model (e.g., a 2D model). Alternatively, the junction effects are corrected for by comparing results of a one-dimensional (1D) casing string model with results of a multi-dimensional casing string model to identify junction effects, and re-processing the EM log data using the 1D casing string model with junction effects removed. Further, multi-stage inversion schemes that correct for junction effects may be employed. For example, multi-stage inversion may include a first stage that inverts a junction location while a casing thickness is fixed, and a second stage that inverts a casing thickness while junction location is fixed using values determined in the first stage. The multi-stage inversion may also include a third stage that inverts a junction location and a casing thickness using values determined in the first and second stages as initial values. Alternatively, multiple iterations of a multi-stage inversion may be performed, where initial values for attributes to be determined for each stage are based on a previous iteration. Further, in different embodiments, the processing operations may apply a layer-sliding inversion and/or a constraint condition that limits an amount of variance between casing thickness results of a 1D casing string model and casing thickness results of a multi-dimensional casing string model.

The processing of EM log data may be performed downhole and/or at earth's surface to derive attributes (e.g., casing thickness, casing conductivity, and/or casing permeability) for a casing string as a function of depth. The derived attributes can further be correlated with one or more types of corrosion and/or with a corrosion index. If corrosion of a particular casing string is determined to exceed a threshold, a corrective action may be performed. Example corrective actions include enhancing, repairing, or replacing at least part of a casing segment. Additionally or alternatively, a treatment can be applied to reduce the rate of corrosion for at least part of a casing segment.

Figure 1B:
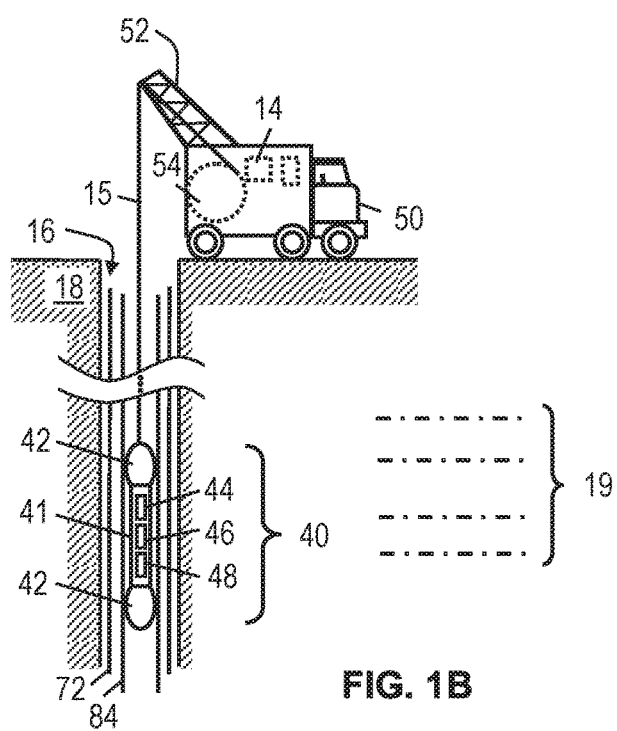

To provide some context for the disclosure, FIGS. 1A and 1B show illustrative casing string survey environments. FIG. 1A shows a permanent well survey environment, where a drilling rig has been used to drill borehole 16 that penetrates formations 19 of the earth 18 in a typical manner. Further, a casing string 72 is positioned in the borehole 16. The casing string 72 of well 70 includes multiple tubular casing segments (usually about 30 feet long) connected end-to-end by couplings 76. It should be noted that FIG. 1C is not to scale, and that casing string 72 typically includes many such couplings 76. Further, the well 70 includes cement slurry 80 that has been injected into the annular space between the outer surface of the casing string 72 and the inner surface of the borehole 16 and allowed to set. Further, a production tubing string 84 has been positioned in an inner bore of the casing string 72. Both the casing string 72 and the production tubing string 84 are formed from multiple segments of metal pipe and are subject to corrosion.

In FIG. 1A, the well 70 corresponds to a production well and is adapted to guide a desired fluid (e.g., oil or gas) from a bottom of the borehole 16 to a surface of the earth 18. Accordingly, perforations 82 may be formed at a bottom of the borehole 16 to facilitate the flow of a fluid 85 from a surrounding formation into the borehole 16 and thence to earth's surface via an opening 86 at the bottom of the production tubing string 84. Note that well configuration of FIG. IA is illustrative and not limiting on the scope of the disclosure. Other examples of permanent well installations include injection wells and monitoring wells. Further, well 70 may include other casing strings in addition to or instead of casing string 72 and production tubing string 84.

In the multi-string EM field survey environment of FIG. 1A, uplink or downlink information is transferred between an EM logging tool (see e.g., FIG. 1B) and a surface interface 14 and/or computer system 20. In some embodiments, the surface interface 14 and/or the computer system 20 may perform various operations such as converting signals from one format to another, storing EM log data collected by an EM logging tool, and/or processing EM log data to determine casing string attributes, where junction effects are corrected for. In at least some embodiments, the computer system 20 includes a processing unit 22 that performs the EM log data analysis operations by executing software or instructions obtained from a local or remote non-transitory computer-readable medium 28. The computer system 20 also may include input device(s) 26 (e.g., a keyboard, mouse, touchpad, etc.) and output device(s) 24 (e.g., a monitor, printer, etc.). Such input device(s) 26 and/or output device(s) 24 provide a user interface that enables an operator to interact with an EM logging tool and/or software executed by the processing unit 22. For example, the computer system 20 may enable an operator to select analysis options, view collected EM log data, view analysis results, and/or perform other tasks.

FIG. 1B illustrates a wireline logging environment in which an EM logging tool 40 is positioned within production tubing string 84 and casing string 72. In FIG. 1B, the EM logging tool 40 is suspended in borehole 16 that penetrates formations 19 of the earth 18. For example, the EM logging tool 40 may be suspended by a cable 15 having conductors and/or optical fibers for conveying power to the EM logging tool 40. The cable 15 may also be used as a. communication interface for uphole and/or downhole communications. In at least some embodiments, the cable 15 wraps and unwraps as needed around cable reel 54 when lowering or raising the EM logging tool 40. As shown, the cable reel 54 may be part of a movable logging facility or vehicle 50 having a cable guide 52.

The EM logging tool 40 includes stabilizers 42 on opposite ends of main body 41 to centralize the tool 40 within the production tubing string 84. The main body 41 of the EM logging tool 40 includes control electronics 44, transmitter(s) 46, and receiver(s) 48. In operation, transmitter(s) 46 are directed by the control electronics 44 to generate a time-varying EM field whose flux is guided by the production tubing string 84 and/or casing string 72. The flux induces a voltage in receiver(s) 48. The flux guide provided by the production tubing string 84 and/or casing string 72 is lossy due to induced eddy currents. The control electronics 44 store the voltages recorded by receiver(s) 48 to form an EM data log, which may be correlated with geometrical, electrical, and/or magnetic attributes of the production tubing string 84 and/or casing string 72. Corrosion of the production tubing string 84 and/or casing string 72 affects their geometrical, electrical, and/or magnetic attributes and can therefore be estimated from analysis of the EM log data. The control electronics 44 may also include a communication interface to transmit the EM data log to earth's surface. Additionally or alternatively, the EM data log obtained by the EM logging tool 40 can be stored and accessed later once the tool 40 reaches earth's surface.

At earth's surface, the surface interface 14 receives the EM data log via the cable 15 and conveys the EM field measurements to a computer system 20. Again, the interface 14 and/or computer system 20 (e.g., part of the movable logging facility or vehicle 50) may perform various operations such as converting signals from one format to another, storing the EM log data, and/or analysis the EM log data to determine casing string attributes, where junction effects are corrected for.

Figures 2A, 2B:
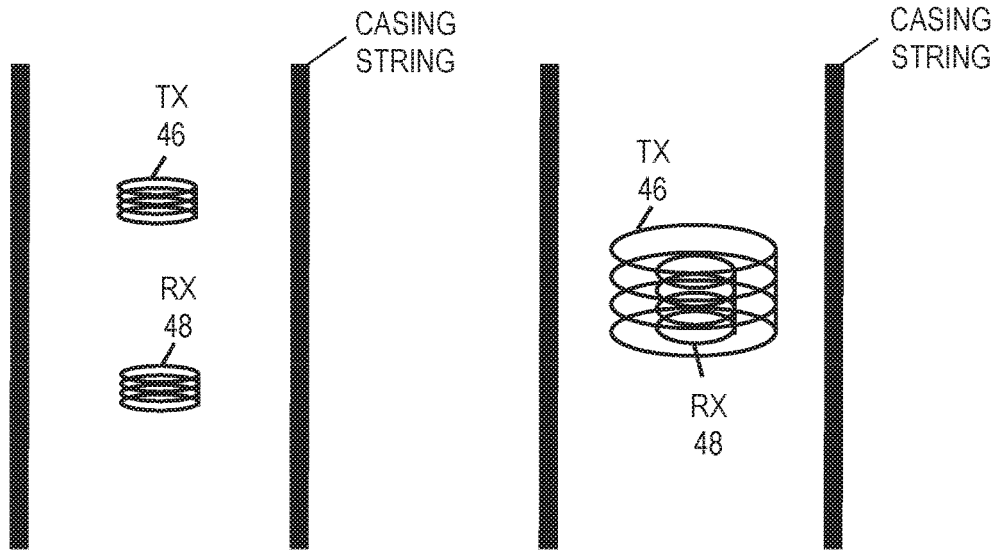
FIGS. 2A and 2B show illustrative transmitter/receiver configurations for an EM logging tool.

FIGS. 2A and 2B show illustrative transmitter/receiver configurations for an EM logging tool (e.g., tool 40). In FIG. 2A, transmitter 46 and receiver 48 are positioned within a casing string (e.g., strings 72 or 84) and are separated. Meanwhile, in FIG. 2B, transmitter 46 and receiver 48 are positioned within a casing string (e.g., strings 72 or 84) and are collocated. For example, transmitter 46 and receiver 48 may correspond to coils or solenoids, where the receiver 48 is positioned inside the transmitter 46, or vice versa. While only one transmitter 46 and one receiver 48 are shown in FIGS. 2A and 2B it should be understood, that EM logging tools such as tool 40 may have a plurality of sensor arrays, where the distance between transmitters 46 and receivers 48 for different sensor arrays may vary. Further, the operation of each sensor arrays may be varied by frequency-domain or time-domain adjustments.

Figure 3A:
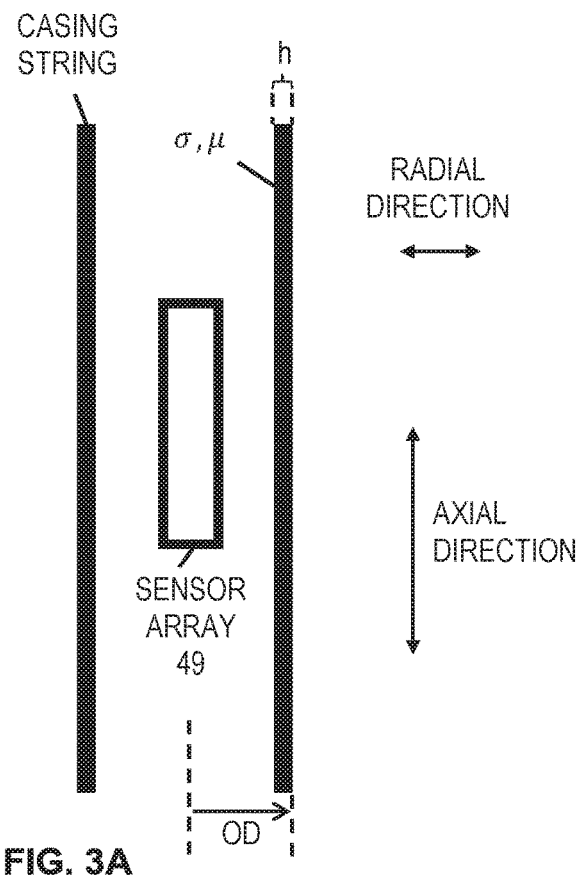
FIG. 3A-3F show illustrative casing string models and/or geometries.

FIGS. 3A-3F shows illustrative casing string models and/or geometries. In FIG. 3A, a sensor array 49 (e.g., one or more transmitter/receiver arrays) is positioned within a casing string. The sensing array 49 may be part of an EM logging tool such as tool 40 to enable various attributes of the casing string (e.g., representative of strings 72 or 84) to be estimated. For the casing string model of FIG. 3A, casing thickness (h), conductivity ($\sigma$), and permeability ($\mu$) are shown to be uniform along the axial direction. If casing materials are known, the attributes to be determined for the casing string of FIG. 3A include the outer diameter (OD), h, $\sigma$, and $\mu$. FIG. 3A represents a 1D casing string model, due to the uniformity of h, $\sigma$, and $\mu$ regardless of axial or radial position.

Figure 3B:
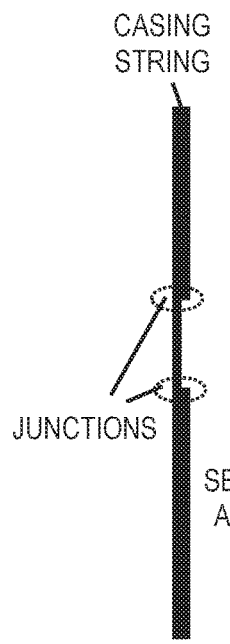
Figure 3C:
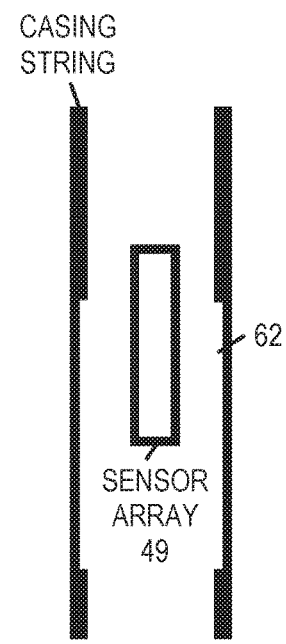
Figure 3D:
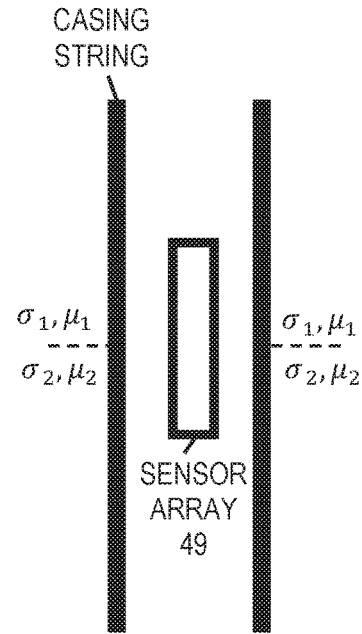

In contrast to the casing string model of FIG. 3A, at least some of the attributes for the casings string models of FIGS. 3B-3F are not uniform as a function of axial position and/or radial position. Thus, FIGS. 3B-3F represent two-dimensional (2D) casing string models. More specifically, the casing string model of FIG. 3B shows a casing string with a small defect 60 (smaller than the size of the sensor array 49), where the thickness of the casing string is not uniform. The thickness non-uniformity along the axial direction of the casing string of FIG. 3B creates junctions (sometimes referred to as "shoulders" where the casing geometry varies) between different sections of the casing string. Note: the term "casing section" used herein is a generic term that refers to any portion of a casing string having multiple segments connected together. Accordingly, the variations in casing string attributes (e.g., Z and h) may or may not occur where casing segments (e.g., 30 ft segments) connect together. Further, the variations in casing string attributes may occur along the length of a single casing segment. Due to its small size relative to the sensor array 49, the defect 60 is difficult to detect as the EM log data is affected by sections of the casing string that are above and/or below the small defect 60. For the casing string model of FIG. 3C, the casing string has a large defect 62 (larger than the size of the sensor array 49). Even so, the defect 62 can be difficult to detect when the sensor array 49 is close to a junction between casing sections with different thicknesses as the EM log data can have contributions from both of the casing sections. The casing string model of FIG. 3D shows a casing string with uniform thickness along the axial direction, but with non-uniform conductivity or permeability. More specifically, the upper section of the casing string in FIG. 3D has conductivity ($\sigma_1$) and permeability ($\mu_1$), while the lower section of the casing string has a different conductivity ($\sigma_2$) and permeability ($\mu_2$).

Figure 3E:
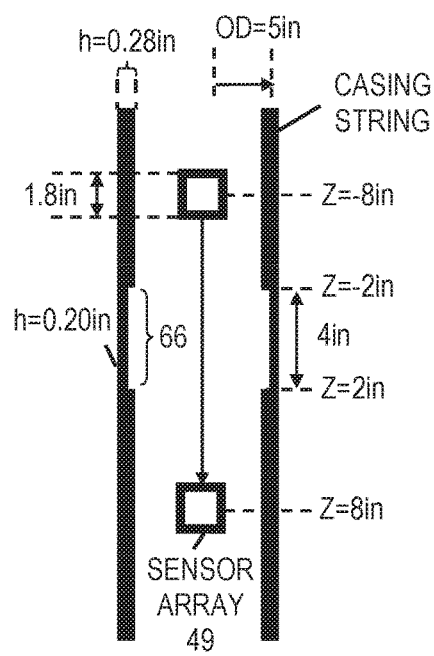
Figure 4:
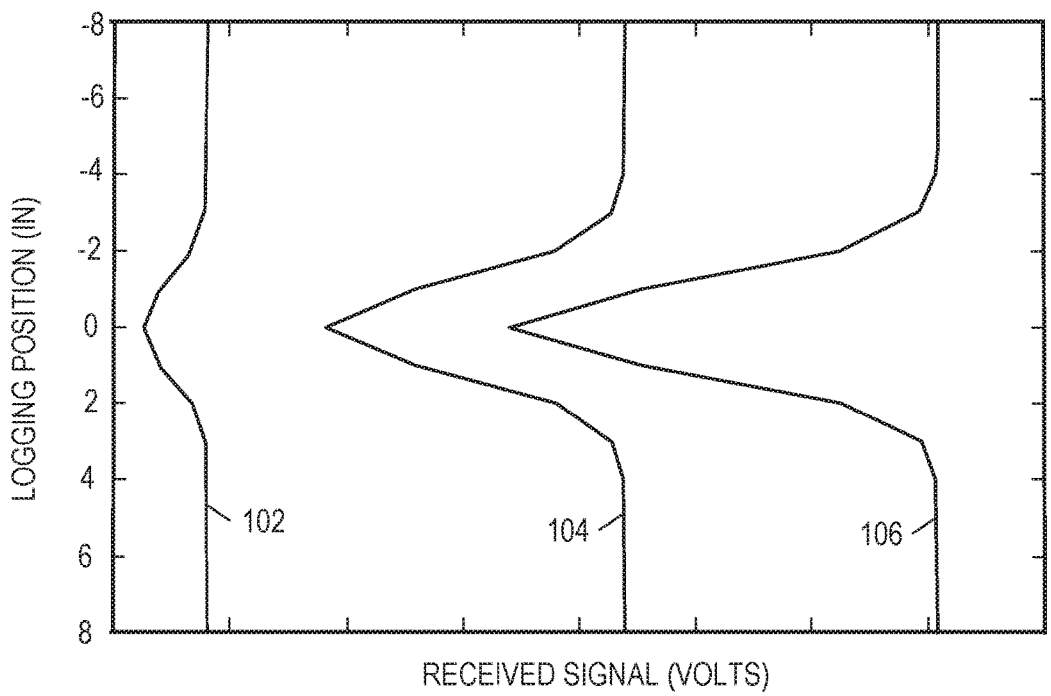
FIG. 4 shows a chart illustrating receiver signal versus logging position.

FIG. 3E shows a synthetic casing string model with attribute values used to generate chart 100 of FIG. 4. For FIG. 3E, the thickness of the casing string is 0.28 inches except in section 66, where the thickness is reduced to 0.20 inches. Further, the outer diameter of the casing string is 5 inches. For the sensor array 49, the transmitter and receiver coils are concentric and are operated in time-domain fashion, where time-decay EM signals are received right after the transmitter is turned off. For the synthetic analysis, the radius of the transmitter is 0.4 inches, the radius of the receiver is 0.35 inches, the casing conductivity is 4,000,000 S/m, and the relative permeability is 100 for the entire casing string. Further, junctions between casing sections with different thicknesses are located at Z=−2 inches and Z=2 inches. When the sensor array 49 moves within the casing string from positions z=−8 inches to z=8 inches, EM data measured at three time bins corresponding to curves 102, 104, and 106 of chart 100 are generated (see FIG. 4). Specifically, curve 102 corresponds to a 12 ms time bin, curve 104 corresponds to a 9 ms time bin, and curve 106 corresponds to a 7 ms time bin. From the chart 100, it can be seen that when the sensor array 49 is close to the junction of different casing sections, the received signals are weighted values (based on the location of the sensor array 49) from contributions from the two different sections.

Figure 3F:
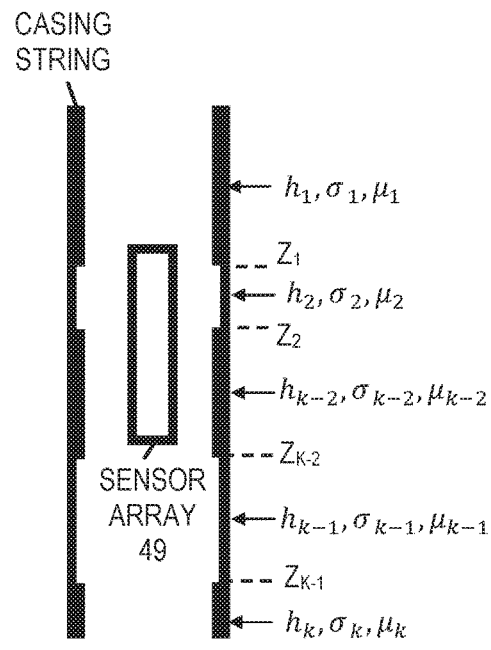

FIG. 3F shows a two-dimensional casing string model, where the casing string has non-uniform thickness, permeability, and/or conductivity along the axial direction. Compared to a 1D casing string model, a two-dimensional casing string model is defined by more parameters or attributes. For the single casing string model given in FIG. 3F, the parameters are OD, $h_j$ (thickness of $j_{th}$ section), and $Z_j$ (boundary between $j_{th}$ and $j+1_{th}$ section), where $1<=j<=k$, and k is the total number of sections with varying thickness. Further, the values $\sigma$ and $\mu$ may vary for each of the k sections. For multi-string scenarios, additional parameters would be used. Further, in some embodiments, a three-dimensional (3D) casing string model may be employed, where casing string attributes (Z, h, $\sigma$, and $\mu$) may vary as a function of axial position, longitudinal position, and/or azimuthal position.

In 1D forward and inversion casing string models, casing thickness is assumed to uniform along the axial direction. If casing materials are known, the attributes to be determined for a casing string include outer diameter ($OD_1$), thickness ($h_1$), conductivity ($\sigma_1$), and permeability ($\mu_1$). To calculate the casing thickness, a numerical optimization (e.g., a Gauss-Newton method) may be employed. In such case, unknown parameters are adjusted until the misfit error between measurement data and predicted data (computed via forward modeling using estimated parameters) are sufficiently small. This goal can be achieved by iteratively solving a non-linear problem that minimizes the objective cost function:

$$C(X) = \tfrac{1}{2}[\|e(X)\|^2], \qquad \text{Equation (1)}$$

where the residual factor is defined as:

$$e(X) = \begin{bmatrix} S_1(X) - m_1 \\ S_2(X) - m_2 \\ \vdots \\ S_j(X) - m_j \\ \vdots \\ S_M(X) - m_M \end{bmatrix}, \qquad \text{Equation (2)}$$

where $S_j(X)$ is the modeled tool response corresponding to a particular value of attribute vector X. For the single casing case, $X=[OD; h; \sigma; \mu]$. If casing OD and casing material are known or predetermined, X is simply equal to casing thickness h, $m_j$ is the corresponding measured data, and $\|.\|$ refers to the L2-norm. If the EM logging tool 40 is operated as a time-domain tool, measured data $m_j$ are usually selected time bins corresponding to different casing diameter. On the other hand, if the EM logging tool 40 is operated at a frequency or multiple frequencies, measured data $m_j$ are collected signals at frequency or frequencies used. If multiple transmitter-receiver arrays are employed in the EM logging tool 40, measured data $m_j$ are tool responses (frequency or time-domain) from all of the selected arrays.

The above scheme corresponding to Equations 1 and 2 can be implemented straightforwardly by using classical optimization methods when the casing thickness and material is close to uniform. However, it becomes inaccurate in other scenarios such as when a small casing defect is present (see e.g., FIG. 3B), when a sensing array is near a junction between different sections (see e.g., FIG. 3C), or when casing conductivity or permeability varies (see e.g., FIG. 3D). When an EM logging tool such as too 40 is close to a junction between casing sections with different geometrical, electrical, and/or magnetic properties, received signals are likely to be affected by both casing sections rather than by just a single casing potion. If a 1D casing string model is used to process the EM log data in the above scenarios, the numerical optimization to determine casing attributes may not be sufficiently accurate.

To overcome the shortcomings of the 1D casing string model for casing corrosion detection, a 2D casing string model (see e.g., FIG. 3F) may be used. For example, Equations 1 and 2 may be employed, where $S_j(X)$ is the modeled tool response corresponding to a particular value of casing attribute vector X. For a 2D casing string model and single casing string scenario, $X=[OD; Z_j; h_j; \sigma_j; \mu_j]$ (see FIG. 3F). If casing OD and casing material are known or predetermined, $X=[Z_j; h_j]$, $m_j$ is the corresponding measured data, and $\|.\|$ refers to the L2-norm. If the EM logging tool 40 is operated as a time-domain tool, measured data $m_j$ are usually selected time bins. On the other hand, if the EM logging tool 40 is operated at a frequency or multiple frequencies, measured data $m_j$ are collected signals at the frequency or frequencies used. If multiple sensor arrays are employed in the EM logging tool 40, measured data $m_j$ are tool responses (frequency or time-domain) from all of the selected arrays. The 2D casing string model given above provides a framework for processing EM log data. Below various processing schemes are described that correct for junction effects by employing a 2D casing string model. Note: a 1D casing string model as described herein is sometimes referred to as 1D processing model, and a 2D casing string model as described herein is sometimes referred to as a 2D processing model. Further, processing using a 1D casing string model is sometimes referred to as 1D processing, while processing using a 2D casing string model is sometimes referred to as 2D processing. Similarly, a multi-dimensional casing string model (e.g., 2D or 3D) may be referred to as a multi-dimensional processing model, and processing using a multi-dimensional casing string model may be referred to as multi-dimensional processing.

Processing Scheme A

Figure 5A:
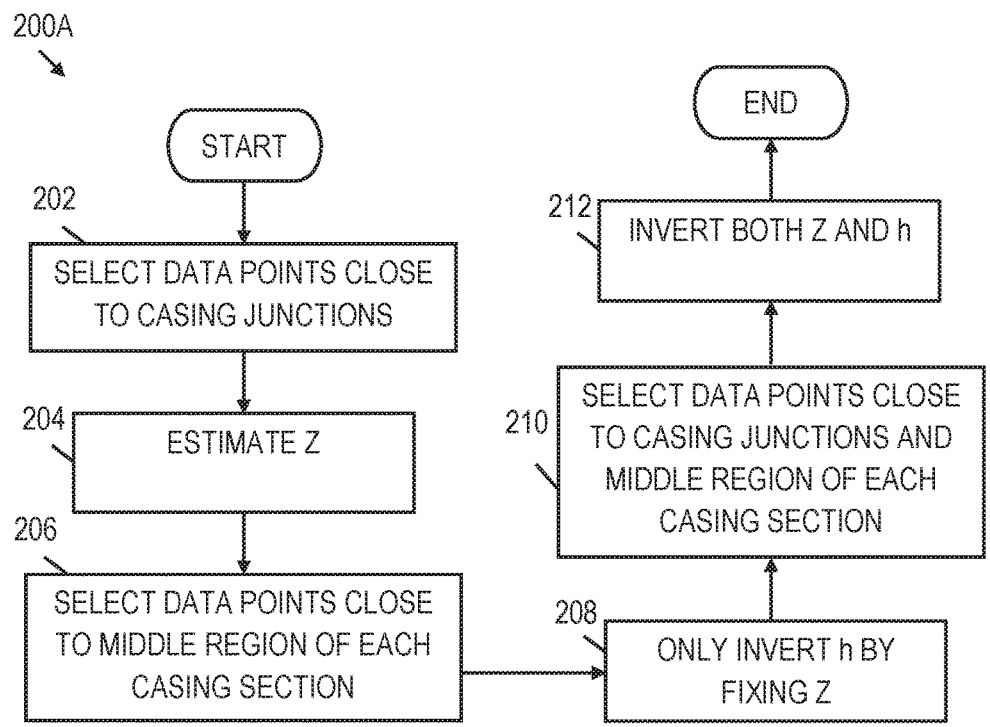
FIGS. 5A-5B show illustrative flowcharts of multi-stage inversion methods that correct for junction effects.
Figure 5B:
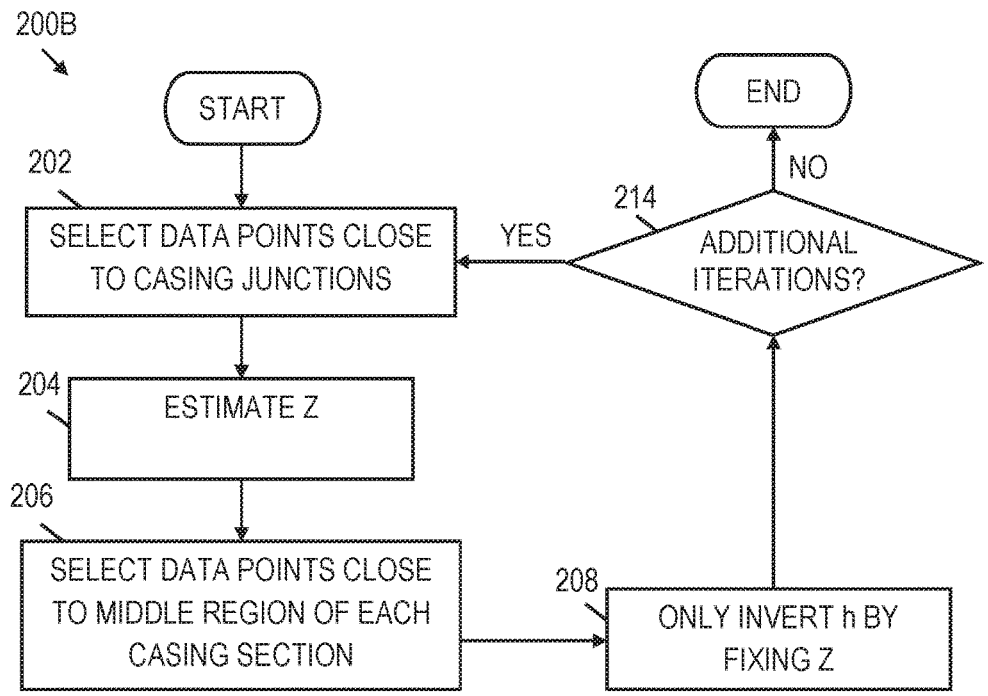

In at least some embodiments, a multi-stage processing scheme (referred to herein as Processing Scheme A) is proposed to produce an accurate estimation of casing thickness. In principle, 1D processing is first conducted to provide approximate results. Then, 2D processing is employed to produce more accurate results that correct for junction effects. The Processing Scheme A (operations A1 to A10) is performed as follows:

A1. Collect logging data.
A2. Start from a first logging position.
A3. Calculate casing thickness using a 1D processing model (e.g., defined by Equations 1 and 2).
A4. Determine if the entire log has been processed. If yes, go to the next operation. Otherwise, go to the next logging position and go back to operation A3.
A5. Once 1D processing is done. Its results are used to detect casing junction locations.
   a. The initial junction locations are determined by a variance based method of a calculated 1D casing thickness forward model (h1d). The variances of h1d at all logging logs are computed within a predefined position window (related to the maximum resolution of the EM logging tool). All logging points with peak value of the variance curve larger than a predefined threshold value are selected as starting boundaries. These starting boundaries are then examined and filtered to ensure that only one bed boundary point can exist within a predefined position window (related to the maximum resolution of the EM logging tool).
   b. The boundaries can also be estimated from initial collected raw logging data. If raw logging data is noise, appropriate smoothing filter has to be applied first.
A6. Create initial 2D processing model using 1D processing results.
   a. To provide an initial 2D processing model, the initial casing thickness and all other unknown parameters are assumed to be same as results from 1D processing. For example, the initial forward model (h2d) is equal to the h1d computed at the middle point of each section.
A7. Select the first processing window.
   a. For real logging processing, a large number of casing sections need to be inverted which will result in a very large inversion problem with many unknowns. Too many unknowns in an inversion model will increase computation complexity and deteriorate inversion accuracy and efficiency. A layer-sliding inversion scheme can be applied. In a layer-sling inversion, a fixed number of layers are modeled in each sub inversion window. After the problem of a sub inversion window is solved, the first layer's formation parameters will be marked as known and removed from the next sub inversion window. Meanwhile, a new layer will be included in the next inversion window. More implementation details for layer-sliding inversions can be found in WO 2014011190 A1, entitled "Method of estimating anisotropic formation resistivity profile using a multi-component induction tool."
   b. Once layer-sliding window scheme is defined, the processing starts from the first window.
A8. Calculate casing thickness using the 2D processing model.
   a. Following the general 2D processing scheme (e.g., defined as Equations 1 and 2 with modified parameters), casing thickness, casing section boundaries along with casing material are iteratively updated until a 2D processing model is obtained which can reproduce measured values.
   b. To enhance the 2D inversion process, a multi-stage inversion scheme can be applied. As used herein, a multi-stage inversion includes multiple stages, where a different casing string attribute or set of attributes is inverted for each stage while other casing string attributes are fixed. For example, assume $X=[Z_j, h_j]$. In the first stage, the $h_j$ values are fixed and only the $Z_j$ values are inverted. Alternatively, the $Z_j$ values may be estimated directed from the received EM data as explained for block 202 of method 200A below. After the $Z_j$ values are calculated, they will be used as fixed values for the next stage. For the second stage, the $Z_j$ values are fixed (using the values determined in the first stage) and only the $h_j$ values are inverted. In a third stage, both $h_j$ and $Z_j$ are inverted using the values determines in the first and second stages as the initial values. At the first stage, measured data at the logging position close to middle region of each section casing are preferred since they are more sensitive to casing thickness. For the second stage, measured data at the logging position close to junctions are preferred since the measured data will be more sensitive to junction effects. Using such a multi-stage inversion scheme, two small-dimension optimization problems are solved first, which usually can provide results close to the final solution. Thus only a few iteration are required to converge to the final solution. Overall, computational efficiency of this multi-stage inversion scheme is better than solving a single large-dimension optimization problem. FIGS. 5A and 5B show illustrative flowcharts of multi-stage inversion methods 200A and 200B that correct for junction effects. The method 200A is related to the processing operation of A8(b) given above. Meanwhile, the method 200B shows a similar approach where additional iterations are employed to perform a sweep update of the first and the second stages. More specifically, the method 200A selects data points close to casing junctions (block 202). As an example, data points close to junctions can be identified by the variance in the received signal exceeding a threshold amount. At block 204, values for Z are estimated. For example, in some embodiments, Z may be estimated from the received data as the locations where variance in the received signal is highest. Alternatively, Z may be estimated by performing an inversion, where only values for Z are inverted while values for h are fixed. At block 206, data points close to a middle region for each casing section are selected. For example, data points close to a middle region for each casing section can be identified by the variance in the received signal being less than a threshold amount. At block 208, only values for h are inverted while values for Z are fixed (e.g., using the values for Z determined in block 204). At block 210, data points close to casing junctions and the middle region of each casing section are selected.

At block 212, values for both Z and h are inverted. The method 200B includes the same blocks 202, 204, 206, and 208 described for method 200A. After block 208, the method 200B determines whether to perform additional iterations (decision block 214). If so, the method 200B repeats blocks 202, 204, 206, and 208, where values determined in a previous iteration are used as the initial values for the attributes to be determined (e.g. Z in block 204, and h in block 208). Once a threshold quality or threshold number of iterations are achieved, the method 200B ends. While, methods 200A and 200B obtain values for Z and h, it should be appreciated that values for $\sigma$ and/or $\mu$ could additionally or alternatively be obtained in a multi-stage inversion. Further, it should be appreciated that the order of the stages may vary (e.g., $\sigma$, $\mu$, and/or h may be determined before Z).

c. To stabilize the 2D inversion process, appropriate constraint conditions are applied.

For example, following term can be added to Equation 2:

$$C_{new}(X) = C(X) + \alpha_j \cdot |h_j^p - h_j^{1d}|^2, \quad \text{Equation (3)}$$

where $C_{new}(X)$ ensures the computed result $h_j^p$ from the 2D processing model is within a threshold amount relative to $h_j^{1d}$ determined from the 1D processing model, where p is the current iteration, j is the casing section number, and $\alpha_j$ is a value determined from numerical experiments.

A9. Determine if all windows have been processed. If yes, go to the next operation. Otherwise, move to the next processing window and go back to operation A8.

A10. Finish.

Figure 6A:
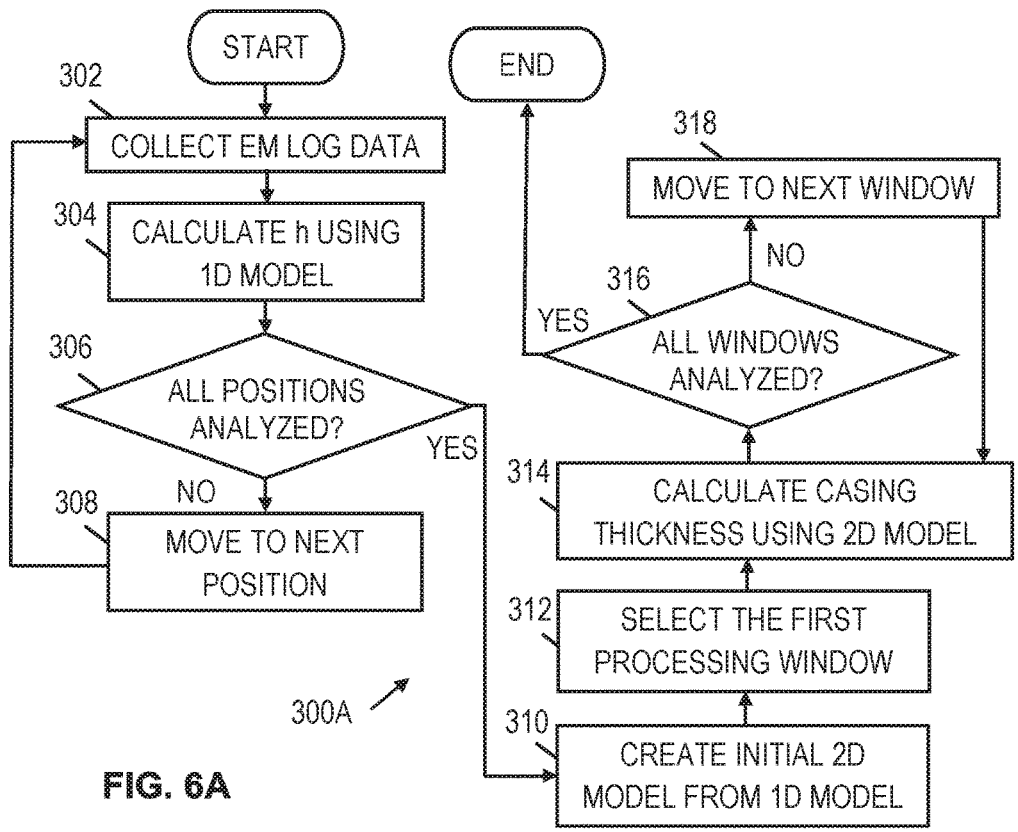
FIGS. 6A and 6B show illustrative flowcharts of processing methods that correct for junction effects.

FIG. 6A shows an illustrative flowchart of a processing method 300A that corrects for junction effects. The method 300A is related to the Processing Scheme A discussed previously. In method 300A. EM log data is collected at block 302. At block 304, values for hare calculated using a 1D processing model. If all logging positions have not been analyzed (decision block 306), the method 300A proceeds to a new position at block 308. Thereafter, blocks 302 and 304 are repeated for the new position. Once all logging positions have been analyzed (decision block 308), an initial 2D processing model is created from the processing model (block 310). At block 312, a first processing window is selected (e.g., a layer-sliding window scheme is employed). At block 314, casing thickness is calculated using the 2D processing model. If all the processing windows have not been analyzed (decision block 316), the method 300A moves to the next processing window (block 318) and block 314 is repeated for the new processing window. Once all the processing windows have been analyzed (decision block 316), the method 300A ends.

Processing Scheme B

An alternative scheme referred to herein as Processing Scheme B can be derived from Processing Scheme A, which is computationally expensive due to the 2D processing model.

To expedite a solution with an acceptable accuracy, the Processing Scheme B performs 1D processing to provide approximate results. Then, an estimated 2D processing model is analyzed to remove junction effects on the original raw data. Subsequently, the raw data is modified to correct for junction effects, and 1D processing is performed again using the modified raw data. The Processing Scheme B is more accurate compared to using a 1D processing model alone and is less computationally expensive than the Processing Scheme A.

The Processing Scheme B (operations B1 to B15) is performed as follows:

B1. Collect logging data.

B2. Start from a first logging position.

B3. Calculate casing thickness using 1D processing model (see Equations 1 and 2).

B4. Determine if the entire log has been processed. If yes, go to the next operation. Otherwise, go to the next logging position and go back to operation B3.

B5. Once 1D processing is done. Its results are used to detect casing junction locations.
  a. The initial junctions are determined by a variance based method of calculated 1D casing thickness in a forward model (h1d). The variances of h1d at all logging logs are computed within a predefined position window (maximum vertical resolution of the tool). All logging points with peak value of the variance curve larger than a predefined threshold value are selected as starting junctions. These starting junctions are then examined and filtered to ensure that only one junction can exist within a predefined position window (related to the maximum resolution of the tool).
  b. The junctions can also be estimated from initial collected raw logging data (see block 204 of methods 200A and 200B). If raw logging data is noise, appropriate smoothing filter has to be applied first.

B6. Create initial 2D processing model using 1D processing results.
  a. To provide the initial model for 2D processing, the initial casing thickness and all other unknown parameters are assumed to be same as results from 1D processing. For example, the initial forward response for the 2D processing model ($h_{2d}$) is equal to the forward response for the 1D processing model ($h_{1d}$) computed at the middle point of each section.

B7. Select the first processing window.
  a. For real logging processing, a large number of casing sections need to be inverted which will result in a very large inversion problem with many unknowns. Too many unknowns in an inversion model will increase computation complexity and deteriorate inversion accuracy and efficiency. Again, a layer-sliding inversion scheme can be applied as described for Processing Scheme A. In this scheme, a fixed number of layers are modeled in each sub inversion window. After the problem of a sub inversion window is solved, the first layer's formation parameters will be marked as known and removed from the next sub inversion window. Meanwhile, a new layer will be included in the next inversion window.
  b. Once layer-sliding window scheme is defined, the processing starts from the first window.

B8. Calculate forward response $f_{2d}$ using estimated 2D processing model.
  a. An estimated 2D processing model has been created from operation B6. The forward response ($f_{2d}$) of such a 2D model with the current window is computed, where $f_{2d}$ is a function of (OD, $Z_j$, $h_j$, $\sigma_j$, $\mu_j$) defined in the current processing window.

B9. Start from the first logging position within the current processing window.

B10. Compute response that corrects for junction effects at current logging position.
  a. The forward response of a 1D model ($f_{1d}$) with the current logging position is first computed, where $f_{1d}$ is a function of (OD, $h_{1d}$, $\sigma_{1d}$, $\mu_{1d}$) defined at the current logging position.

b. Then, response that corrects for junction effects can be computed from the following equation:

$$m_j^{corrected} = m_j^{raw} + (f_{1d} - f_{2d}),\quad \text{Equation (4)}$$

B11. Calculate casing thickness using corrected raw data $m_j^{corrected}$ and 1D processing model (see Equations 1 and 2). Certainly, already estimated parameters (from operation B2 to operation B4) can be taken as initial guess values for 1D processing.

B12. Determine if all logging positions have been processed. If yes, go to the next operation. Otherwise, go to the next logging position and go back to operation B11.

B13. Determine if all windows have been processed. If yes, go to the next operation. Otherwise, move to the next processing window and go back to operation B8.

B14. If additional iteration is desired, then go to operation B2. Otherwise, go to the next operation.
  a. Since this scheme does not use a 2D processing model to compute casing thickness, its accuracy is not good as the previous scheme. In addition, using Equation 4 cannot totally remove junction effects because both 1D and 2D processing models used to calculate forward response may not be accurate enough. To address this potential issue, additional iterations can be utilized to improve its accuracy, by further removing junction effects.

B15. Finish.

Figure 6B:
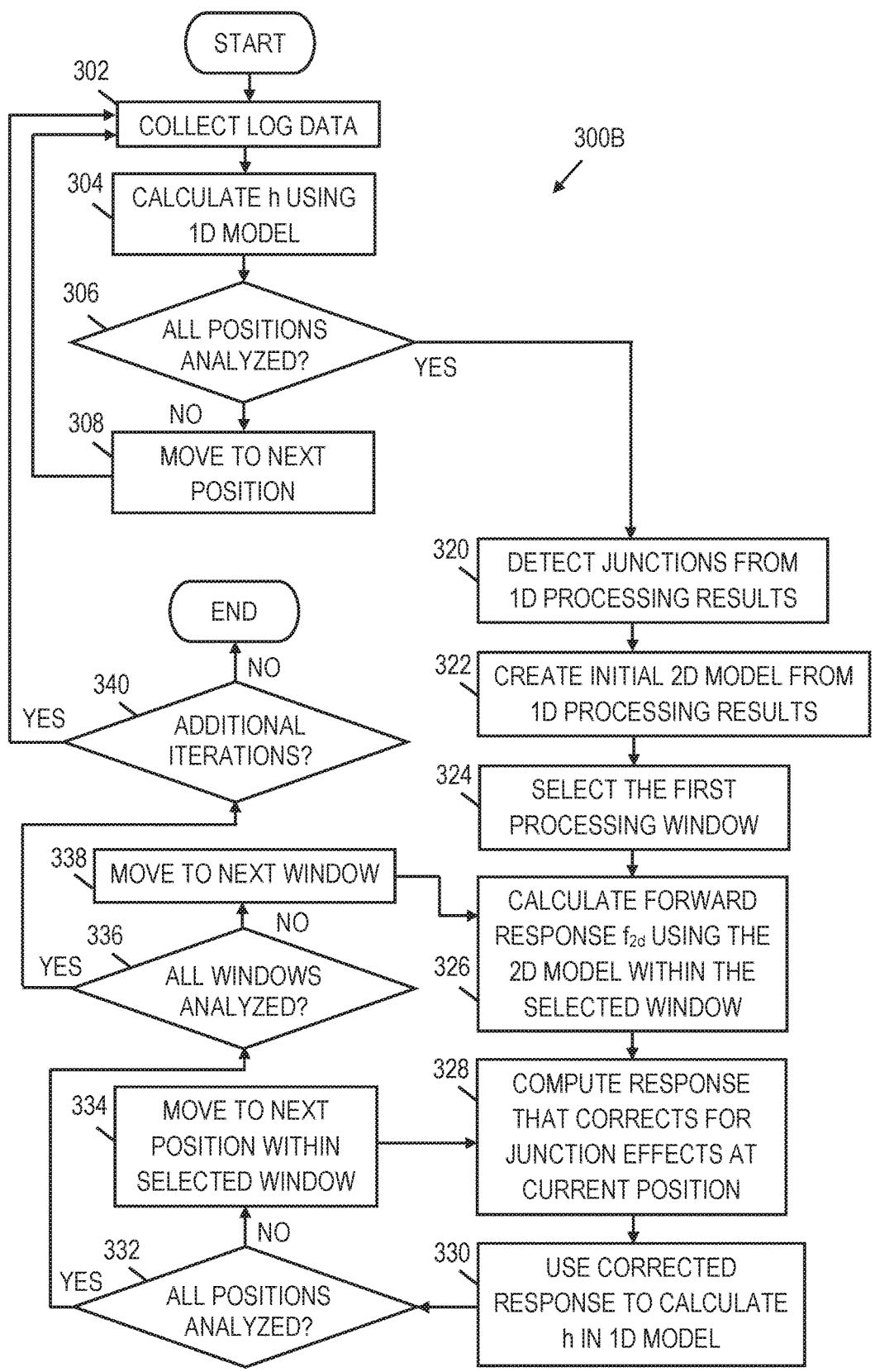

FIG. 6B shows an illustrative flowchart of a processing method 300B that corrects for junction effects. The method 300B is related to the Processing Scheme B discussed previously. In method 300B, blocks 302, 304, 306, and 308 are the same as the method 300A of FIG. 6A. Once all positions have been analyzed (decision block 308), junction locations are detected from the 1D processing results (block 320). At block 322 an initial 2D model is created from the 2D processing results. At block 324, a first processing window is selected (e.g., a layer-sliding window scheme is employed). At block 326, a forward response ($f_{2d}$) using the 2D model is calculated within the selected processing window. At block 328, a response that corrects for junction effects is computed at the current logging position. At block 330, the corrected response is used to calculate h in a 1D model.

After block 330, the method 300B determines whether all logging positions have been analyzed (decision block 332). If not, the method 300B proceeds to a next logging position within the selected processing window (block 334), and repeats blocks 328 and 330. If all logging positions have been analyzed (decision block 332), the method 300B determines is all processing windows have been analyzed (decision block 336). If not, the method 300B proceed to a next processing window (block 338), and repeats blocks 326, 328, and 330. If all processing windows have been analyzed (decision block 336), the method 300B determines whether to perform additional iterations (decision block 340). If not, the method 300B ends. Otherwise, the method 300B returns to block 302 to perform another iteration. The method 300B may perform additional iterations until a quality threshold or iteration count is reached.

Embodiments disclosed herein include:
A: A corrosion monitoring method that comprises obtaining EM log data along a casing string, and processing the EM log data to estimate casing thickness of the casing string as a function of position. The processing corrects for junction effects in the casing string.
B: A corrosion monitoring system that comprises an EM logging tool to collect EM log data along a casing string, and a processing unit in communication with the EM logging tool. The processing unit processes the EM log data to estimate casing thickness of the casing string as a function of position, wherein the processing unit corrects for junction effects in the casing string.

Each of the embodiments, A and B, may have one or more of the following additional elements in any combination. Element 1: correcting for junction effects in the casing string comprises employing a multi-dimensional casing string model. Element 2: correcting for junction effects further comprises applying a multi-stage inversion with multiple stages, where a different casing string attribute or set of attributes is inverted for each stage while at least one other casing string attribute is fixed. Element 3: the multi-stage inversion comprises a first stage that inverts a junction location while a casing thickness is fixed, and a second stage that inverts a casing thickness while junction location is fixed using values determined in the first stage. Element 4: the multi-stage invention further comprises selecting EM log data at or near a casing junction for the first stage, and selecting EM log data at or near a middle region of a casing section for the second stage. Element 5: the multi-stage inversion further comprises a third stage that inverts a junction location and a casing thickness using values determined in the first and second stages as initial values. Element 6: the multi-stage inversion further comprises performing multiple iterations of the multi-stage inversion, where initial values for attributes to be determined for each stage are based on a previous iteration. Element 7: correcting for junction effects in the casing string comprises comparing results from a 1D casing string model and a multi-dimensional casing string model to identify the junction effects, and re-processing the EM log data using the 1D casing string model with the junction effects removed. Element 8: correcting for junction effects in the casing string comprises estimating junction positions directly from the EM log data, and inverting at least one other casing string attribute while a junction position attribute based on said estimating is fixed. Element 9: correcting for junction effects in the casing string comprises calculating a first forward response using the multi-dimensional model and a second forward response using the 1D model, and wherein comparing results comprises comparing the first and second forward responses. Element 10: correcting for junction effects in the casing string comprises using a 1D model to identify one or more casing string attributes, and setting values for a multi-dimensional model based on the one or more casing string attributes determined using the 1D model. Element 11: correcting for junction effects in the casing string comprises applying a layer-sliding inversion. Element 12: correcting for junction effects in the casing string comprises applying a constraint condition that limits an amount of variance between casing thickness results of a 1D casing string model and casing thickness results of a multi-dimensional casing string model.

Element 13: the processing unit corrects for junction effects in the casing string by performing a multi-stage inversion with multiple stages, where a different casing string attribute or set of attributes is inverted for each stage while at least one other casing string attribute is fixed. Element 14: the multi-stage inversion further comprises a stage that inverts a junction location and a casing thickness using values determined in previous stages as initial values. Element 15: the processing unit performs multiple iterations of the multi-stage inversion, where initial values for attributes to be determined for each stage are based on a previous iteration. Element 16: the processing unit accounts for junction effects in the casing string by comparing results from two different models to identify the junction effects, and Re-processing the EM log data using one of the different models with the junction effects removed. Element 17: the processing unit corrects for junction effects in the casing string based on a multi-dimensional casing string model. Element 18: the processing unit corrects for junction effects in the casing string by applying at least one of a layer-sliding inversion, and a constraint condition that limits an amount of variance between casing thickness results of a 1D model and casing thickness results of a multi-dimensional model.

Numerous other variations and modifications will become apparent to those skilled in the art once the above disclosure is fully appreciated. For example, the disclosed inversion schemes can be extended to two-string, three-string, four-string, or other multi-string scenarios as needed. Further, in some embodiments, the order of the processing operations described herein may vary and/or be performed in parallel. It is intended that the following claims be interpreted to embrace all such variations and modifications where applicable.

What is claimed:

1. A corrosion monitoring method that comprises:
   disposing an electromagnetic (EM) logging tool downhole;
   generating a time-varying EM field along a casing string with a transmitter, wherein the transmitter is a coil or a solenoid;
   recording a voltage induced by the EM field with a receiver, wherein the receiver is a coil or a solenoid;
   constructing an EM data log with the recorded voltage; and
   processing the EM data log to estimate casing thickness of the casing string as a function of position, wherein said processing comprises correcting for junction effects in the casing string, wherein the correcting for junction effects in the casing string comprises:
      comparing results from a one-dimensional (1D) casing string model and a multi-dimensional casing string model to identify the junction effects; and
      re-processing the EM log data using the 1D casing string model with the junction effects removed.

2. The method of claim 1, wherein said correcting for junction effects in the casing string comprises employing a multi-dimensional casing string model.

3. The method of claim 2, wherein said correcting for junction effects further comprises applying a multi-stage inversion with multiple stages, where a different casing string attribute or set of attributes is inverted for each stage while at least one other casing string attribute is fixed.

4. The method of claim 3, wherein the multi-stage inversion comprises:
   a first stage that inverts a junction location while a casing thickness is fixed; and
   a second stage that inverts a casing thickness while junction location is fixed using values determined in the first stage.

5. The method of claim 4, further comprising:
   selecting EM log data at or near a casing junction for the first stage; and
   selecting EM log data at or near a middle region of a casing section for the second stage.

6. The method of claim 4, wherein the multi-stage inversion further comprises a third stage that inverts a junction location and a casing thickness using values determined in the first and second stages as initial values.

7. The method of claim 4, wherein the multi-stage inversion further comprises performing multiple iterations of the multi-stage inversion, where initial values for attributes to be determined for each stage are based on a previous iteration.

8. The method of claim 1, wherein said correcting for junction effects in the casing string comprises estimating junction positions directly from the EM log data, and inverting at least one other casing string attribute while a junction position attribute based on said estimating is fixed.

9. The method of claim 1, wherein said correcting for junction effects in the casing string comprises calculating a first forward response using the multi-dimensional model and a second forward response using the 1D model, and wherein comparing results comprises comparing the first and second forward responses.

10. The method of claim 1, wherein said correcting for junction effects in the casing string comprises using a one-dimensional (1D) model to identify one or more casing string attributes, and setting values for a multi-dimensional model based on the one or more casing string attributes determined using the 1D model.

11. The method of claim 1, wherein said correcting for junction effects in the casing string comprises applying a layer-sliding inversion.

12. The method of claim 1, wherein said correcting for junction effects in the casing string comprises applying a constraint condition that limits an amount of variance between casing thickness results of a one-dimensional (1D) casing string model and casing thickness results of a multi-dimensional casing string model.

13. A corrosion monitoring system that comprises:
   an electromagnetic (EM) logging tool to collect EM log data along a casing string, wherein the EM logging tool comprises:
      a transmitter, wherein the transmitter generates a time-varying EM field, wherein the transmitter is a coil or a solenoid; and
      a receiver, wherein the receiver records a voltage induced by the EM field, wherein the receiver is a coil or a solenoid; and
   a processing unit in communication with the EM logging tool, wherein the processing unit processes the EM log data to estimate casing thickness of the casing string as a function of position, wherein the processing unit corrects for junction effects in the casing string by:
      comparing results from two different models to identify the junction effects; and
      re-processing the EM log data using one of the different models with the junction effects removed.

14. The system of claim 13, wherein the processing unit corrects for junction effects in the casing string by performing a multi-stage inversion with multiple stages, where a different casing string attribute or set of attributes is inverted for each stage while at least one other casing string attribute is fixed.

15. The system of claim 14, wherein the multi-stage inversion further comprises a stage that inverts a junction location and a casing thickness using values determined in previous stages as initial values.

16. The system of claim 14, wherein the processing unit performs multiple iterations of the multi-stage inversion, where initial values for attributes to be determined for each stage are based on a previous iteration.

17. The system of claim 13, wherein said processing unit corrects for junction effects in the casing string based on a multi-dimensional casing string model.

18. The system of claim 13, wherein said processing unit corrects for junction effects in the casing string by applying at least one of a layer-sliding inversion, and a constraint condition that limits an amount of variance between casing thickness results of a one-dimensional (1D) model and casing thickness results of a multi-dimensional model.

19. A corrosion monitoring method that comprises:
disposing an electromagnetic (EM) logging tool downhole;
generating a time-varying EM field along a casing string with a transmitter, wherein the transmitter is a coil or a solenoid;
recording a voltage induced by the EM field with a receiver, wherein the receiver is a coil or a solenoid
constructing an EM data log with the recorded voltage; and
processing the EM data log to estimate casing thickness of the casing string as a function of position, wherein said processing comprises correcting for junction effects in the casing string, wherein said correcting for junction effects in the casing string comprises:
employing a multi-dimensional casing string model;
applying a multi-stage inversion with multiple stages, where a different casing string attribute or set of attributes is inverted for each stage while at least one other casing string attribute is fixed, wherein the multi-stage inversion comprises a first stage that inverts a junction location while a casing thickness is fixed and a second stage that inverts a casing thickness while the junction location is fixed using values determined in the first stage;
selecting EM log data at or near a casing junction for the first stage; and
selecting EM log data at or near a middle region of a casing section for the second stage.

* * * * *